United States Patent
Hussain et al.

(10) Patent No.: US 8,034,986 B2
(45) Date of Patent: Oct. 11, 2011

(54) PROCESSING OF SOLID BROMINATED AROMATIC ORGANIC COMPOUNDS CONTAINING OCCLUDED BROMINE

(75) Inventors: Saadat Hussain, Baton Rouge, LA (US); Arthur G. Mack, Prairieville, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 11/840,302

(22) Filed: Aug. 17, 2007

(65) Prior Publication Data

US 2008/0114195 A1  May 15, 2008

Related U.S. Application Data

(60) Provisional application No. 60/865,121, filed on Nov. 9, 2006.

(51) Int. Cl.
- C07C 17/38 (2006.01)
- C07C 25/00 (2006.01)
- C07C 17/00 (2006.01)

(52) U.S. Cl. .................. 570/211; 570/184; 570/206

(58) Field of Classification Search .............. None
See application file for complete search history.

(56) References Cited

U.S. PATENT DOCUMENTS

| | | | |
|---|---|---|---|
| 3,752,856 A | 8/1973 | Nagy et at. |
| 3,965,197 A | 6/1976 | Stepniczka |
| 4,847,428 A | 7/1989 | Gu |
| 5,008,477 A | 4/1991 | Hussain |
| 5,030,778 A | 7/1991 | Ransford |
| 5,077,334 A | 12/1991 | Hussain |
| 5,124,496 A | 6/1992 | Templeton et al. |
| 5,302,768 A | 4/1994 | Hussain |
| 5,324,874 A | 6/1994 | Ransford et al. |
| 5,401,890 A | 3/1995 | Parks |
| 5,457,248 A | 10/1995 | Mack et al. |
| 5,741,949 A | 4/1998 | Mack |
| 6,008,283 A | 12/1999 | Rose et al. |
| 6,518,468 B1 | 2/2003 | Parks et al. |
| 6,603,049 B1 | 8/2003 | Parks et al. |
| 6,768,033 B2 | 7/2004 | Parks et al. |
| 6,841,702 B2 | 1/2005 | Magdolen et al. |
| 6,958,423 B2 | 10/2005 | Parks et al. |
| 6,974,887 B2 | 12/2005 | Parks et al. |
| 7,129,385 B2 | 10/2006 | Dawson et al. |
| 2003/0144563 A1 | 7/2003 | Falloon et al. |
| 2004/0110996 A1 | 6/2004 | Parks et al. |

FOREIGN PATENT DOCUMENTS

| | | | |
|---|---|---|---|
| CA | 2094469 | | 9/2005 |
| CN | 1429800 | | 7/2003 |
| DE | 2400455 A1 | | 2/1975 |
| DE | 2950877 A1 | | 6/1981 |
| DE | 3326343 | | 1/1985 |
| EP | 0107978 A1 | | 5/1984 |
| EP | 0347116 A2 | | 12/1989 |
| EP | 0445595 A2 | | 9/1991 |
| EP | 0571859 A2 | | 12/1993 |
| GB | 981833 | | 1/1965 |
| GB | 1411524 | | 10/1975 |
| GB | 2143521 | * | 2/1985 |
| JP | 50018430 | | 2/1975 |
| JP | 52039639 | | 3/1977 |
| JP | 52139033 | | 11/1977 |
| JP | 53053629 | | 5/1978 |
| JP | 53116332 | | 10/1978 |
| JP | 54044623 | | 4/1979 |
| JP | 58222043 | | 12/1983 |
| JP | 62004241 | * | 1/1987 |
| JP | 10158202 | | 6/1998 |
| JP | 10175893 | | 6/1998 |
| WO | WO 93/24434 A1 | | 12/1993 |
| WO | WO 94/22978 A1 | | 10/1994 |
| WO | WO 03/055832 A1 | | 7/2003 |

OTHER PUBLICATIONS

Yang, Ze-hui, et al., "Technological Progress in Catalytic Synthesis of Decabromodiphenyl Ether by Brominating Diphenyl Oxide with Bromine Chloride", Fine Chemicals, vol. 19, Jan. 2002, pp. 42-44, abstract only translated.

Albemarle Corporation, XP002458574, Saytex 8010 Flame Retardant, Brochure, 2001, 2 pages.

* cited by examiner

*Primary Examiner* — Karl J Puttlitz
(74) *Attorney, Agent, or Firm* — Jeremy J. Kliebert

(57) ABSTRACT

Solid-state highly brominated compounds such as solid brominated flame retardants with bromine contents of at least about 60 wt % often contain occluded bromine. Because of their high bromine contents, such compounds have relatively low solubility in common organic solvents. Despite this low solubility, the content of occluded bromine in such solid brominated compounds is effectively reduced by agitating a concentrated agitated slurry of the compound in an inert solvent at a suitable temperature for at least about 1 hour. Thereafter, solids with reduced content of occluded bromine are isolated or recovered from the slurry. Novel products having substantially reduced or eliminated occluded bromine contents and other very desirable characteristics are also provided.

16 Claims, No Drawings

PROCESSING OF SOLID BROMINATED AROMATIC ORGANIC COMPOUNDS CONTAINING OCCLUDED BROMINE

REFERENCE TO RELATED APPLICATION

This application claims benefit and priority of U.S. Provisional Application No. 60/865,121, filed Nov. 9, 2006, the disclosure of which is incorporated herein by reference.

TECHNICAL FIELD

This invention relates to processes for reducing the occluded bromine content of solid, highly brominated aromatic organic compounds, especially of decabromodiphenylethane products. This invention also relates to production and provision of novel, improved decabromodiphenylethane products.

BACKGROUND

Various solid, highly brominated aromatic organic compounds, i.e., compounds which contain at least about 60 wt % of total bromine, are useful, e.g., as flame retardants for thermoplastic and/or thermosetting polymeric resins, or for other flammable materials. Such compounds are usually formed by bromination of the unbrominated aromatic compound with excess bromine in the presence of a bromination catalyst and in a reaction mixture having a liquid phase which may be excess bromine itself. Unfortunately, many such highly brominated compounds formed in this manner, also have elemental bromine trapped within their particles or crystals. Such bromine is often referred to as occluded bromine. The presence of such bromine in the compound is undesirable because the entrapped bromine imparts color to the particles, and can lower the thermal stability of the flame retardant and of the polymer in which the flame retardant is used. Also during thermal processing of thermoplastic polymers containing such highly brominated compounds as flame retardants, bromine and/or HBr can be released and these substances are highly corrosive to materials used in the fabrication of such processing equipment.

Because these highly brominated aromatic compounds have poor solubility in common organic solvents, it is not economically feasible to purify the compounds by typical washing or recrystallization procedures. Too much solvent would be required.

U.S. Pat. Nos. 6,518,468; 6,603,049; 6,768,033; 6,958,423; and 6,974,887 describe, inter alia, commercially-used process technology for effectively reducing the occluded bromine content of decabromodiphenylethane product, one of the commercially important members of the highly brominated aromatic organic compounds with which this invention is concerned. That process technology involves oven-aging at elevated temperatures, previously ground and dried product.

U.S. Pat. No. 5,457,248 describes as one of its features, a high temperature aromatic solvent treatment of a brominated diphenylalkane to improve its color characteristics. It is pointed out that the aromatic solvent used in such high temperature treatment must not decompose at the temperatures at which the brominated diphenylalkane dissolves in the solvent. Such temperatures are stated to be, typically, in excess of 175° C. and often in excess of 200° C., e.g., usually about 200° C. to about 300° C. To perform such high temperature treatment, the brominated diphenylalkane is contacted with the aromatic solvent at a temperature sufficiently high that the brominated diphenylalkane is dissolved in the solvent, preferably forming a solution essentially free of solid diphenylalkane material. Preferred aromatic solvents are indicated to be non-fused aromatic compounds such as biphenyls, diphenylalkanes, (e.g. with $C_1$ to $C_{10}$ alkylene bridges), diphenyloxides, diphenylsufones, diphenylcarbonates, and the like, as well as fused aromatic solvents such as naphthalene or naphthalene derivatives such as alkyl naphthalenes. After complete dissolution of the brominated diphenylalkane, the solution is caused to be at a temperature at which the brominated diphenylalkane precipitates. Although it is stated that high product recoveries can be readily achieved, the primary figure given is 75% or more. Although recoveries ranging even up to about 90 to 95 wt % or more are mentioned, it appears that at least some loss of product is to be expected by use of the solvent process of this patent. Also, because many of the aromatic solvents, including the preferred diphenylalkanes and diphenyloxide, are solids at room temperature, special procedures are recommended to effect separation between the brominated diphenylalkanes and the aromatic solvent. One such procedure includes hot filtration to avoid solidification of the solvent itself along with the brominated product. Another such procedure includes allowing both the aromatic solvent and the brominated diphenylalkane to solidify. The resultant solid mixture can then be treated with another liquid organic solvent in which the solid solvent material, but not the brominated diphenylalkane product, is soluble. The brominated diphenylalkane product can then be filtered from the resulting medium. In conducting the high temperature aromatic solvent procedure of the patent, the special hot filtration procedure was used and in each such case the filtrate resulting from the high temperature filtration was washed with an ordinary organic solvent (methanol or acetone), the filtrate was reslurried in the same solvent and filtered, and this filtrate was washed with the same solvent. Obviously such special procedures add to the complexity and costs of the process.

Thus, procedures used heretofore for reducing occluded bromine content involved roasting the compounds at high temperatures or dissolving the compounds in a solvent at high temperature and then precipitating the compounds out of solution at lower temperatures. It would be of advantage if less complex and less costly procedures for achieving reductions in occluded bromine content could be found.

BRIEF SUMMARY OF THE INVENTION

This invention provides new, low-cost, alternative process technology enabling efficient reduction of the occluded bromine content of solid highly brominated aromatic organic compounds which contain at least about 60 wt % of total bromine. The process technology of this invention is particularly effective for removing occluded bromine content from decabromodiphenylethane products, especially decabromodiphenylethane products formed by brominating diphenylethane in a liquid phase consisting essentially of excess bromine. Typically, such a bromination process utilizes an aluminum catalyst which can be in the form of aluminum foil, aluminum powder, or other subdivided forms of aluminum metal or aluminum alloys. Preferably, however, an aluminum halide catalyst is employed and such catalyst is typically charged to the solvent when in the form of aluminum chloride or aluminum bromide. In other embodiments, this invention provides novel and improved decabromodiphenylethane products and process technology for their production.

The process technology of this invention enables reductions in the content of occluded bromine in highly brominated, particulate organic compounds that have poor solubility in organic solvents. The particle size of the particulate organic compounds used in this process technology is not critical. Such compounds can be in the size range of from very fine powders up to coarse particles or grains having, say, a mean particle size of about 300 microns.

Pursuant to one of the embodiments of this invention, there is provided a process of reducing the content of occluded bromine in at least one particulate brominated organic compound that has a total bromine content of at least about 60 wt % (preferably at least about 70 wt %) and that contains occluded bromine, which process comprises heating for a period of at least about 1 hour, a concentrated agitated slurry of such compound(s) in an inert organic liquid diluent at one or more temperatures in the range of about 60° C. up to the temperature that is just below the temperature at which thermal decomposition of said at least one particulate brominated organic compound begins to occur, the occluded bromine content of the resultant solids being reduced in the process, the amount of dissolved brominated organic compound being treated in the process not exceeding about 5 wt % in the liquid phase at any time during said period.

Determination of the weight percentage of dissolved brominated organic compound in the slurry at any given point of time can be accomplished as follows:
a) briefly discontinue the agitation of the slurry;
b) take a known quantity of a representative sample of the slurry at the slurry temperature;
c) filter the slurry at the slurry temperature;
d) weigh the filtrated at the slurry temperature;
e) reduce the temperature of the filtrate to room temperature (about 25° C.), which causes dissolved brominated organic compound to precipitate;
f) recover the precipitated solids by filtration; and
g) dry and weigh the recovered precipitated solids.

The weight of these recovered precipitated solids from the sample represents the weight of the dissolved brominated organic compound at the reaction temperature in the filtrate, from which a percentage of dissolved brominated organic compound can be readily calculated.

Desirably, the resultant solids are recovered from the slurry by use of a physical separation procedure such as filtration, centrifugation, draining, or the like. Prior to isolating solids from the slurry, the slurry can be cooled or allowed to cool to a temperature that is lower than the temperature(s) to which the agitated slurry was exposed.

In another process embodiment of this invention, prior to conducting the above slurrying process, said at least one particulate brominated organic compound that has a total bromine content of at least about 60 wt % and that contains occluded bromine is heated while in the form of a particulate solid-state compound at a temperature in the range of about 150 to about 230° C. for a period in the range of about 3 to about 6 hours, and is then subjected to the above slurrying process. In still another process embodiment of this invention, after conducting the above slurrying process, solids of said at least one particulate brominated organic compound that has a total bromine content of at least about 60 wt % are recovered from the slurry and are heated at a temperature in the range of about 150 to about 230° C. for a period in the range of about 3 to about 6 hours.

The amount of occluded bromine in the brominated organic compound to be subjected to a process of this invention is not critical to operability. Any amount can be present. The amount of occluded bromine in such brominated organic compound only comes into consideration when evaluating the economics of a given situation. If it makes economic sense to reduce the amount of occluded bromine present in the compound to a lower level or to eliminate it altogether, it is desirable to employ the process. But if the amount of occluded bromine present is small enough to be of no concern to the end user, then the economics would tend to mitigate against use of the process.

As used herein including the claims, the term "occluded bromine" means free, elemental bromine which is tightly held within the particles of the compound such that such bromine is not removed from the compound by conventional washing of the product with water or with a typical organic solvent on a filter. Also, as used herein, including the claims, the term "concentrated" with respect to the slurry whether or agitated or not, means that the slurry contains at least about 20 volume percent of the brominated organic compound(s) being subjected to the process.

Preferred embodiments of this invention are processes that not only reduce the content of occluded bromine in a particulate decabromodiphenylethane product that contains occluded bromine, but that in addition, enable preparation of particulate decabromodiphenylethane products of this invention having a novel combination of desirable properties. The decabromodiphenylethane product used in these preferred processes will typically contain in the range of about 98 to about 99.9 GC area percent of decabromodiphenylethane and nonabromodiphenylethane in an amount in the range of about 0.1 to about 2 GC area percent. A smaller amount of octabromodiphenylethane as determined by GC may also be present in the product, in which case the amount of nonabromodiphenylethane will be less than about 2 GC area percent.

One such preferred process, which is sometimes referred to hereinafter as the heating-slurrying process, comprises:
heating the particulate solid-state decabromodiphenylethane product at a temperature in the range of about 150 to about 230° C. and for a period of at least about 3 to about 6 hours; and
forming from decabromodiphenylethane product that was subjected to said heating, a concentrated agitated slurry in an inert organic liquid diluent at one or more temperatures in the range of about 60° C. up to the temperature that is just below the temperature at which thermal decomposition of the decabromodiphenylethane product begins, the occluded bromine content of the resultant solids being reduced in the process, said slurry containing during said period no more than about 5 wt % (preferably no more than about 3 wt %) of dissolved decabromodiphenylethane product being treated in the process. Before forming the concentrated slurry, the heated compound can be cooled or allowed to cool or it can be directly introduced while hot into the inert organic liquid diluent.

Another such preferred process, which is sometimes referred to hereinafter as the slurrying-heating process, comprises:
forming from decabromodiphenylethane product, a concentrated agitated slurry in an inert organic liquid diluent and heating such slurry at one or more temperatures in the range of about 60° C. up to the temperature that is just below the temperature at which thermal decomposition of the decabromodiphenylethane product begins, the occluded bromine content of the resultant particulate solids being reduced in the process, said slurry containing during said period no more than about 5 wt % (preferably no more than about 3 wt %) of dissolved decabromodiphenylethane product being treated in the process; and
recovering resultant particulate solids from the slurry and heating such particulate solids at a temperature in the range of about 150 to about 230° C. and for a period of at least about 3 to about 6 hours.

Since the amount of one or more minor constituents of the product, e.g., constituents such as nonabromodiphenylethane, octabromodiphenylethane, etc., can have an effect upon the temperature at which thermal decomposition of the decabromodiphenylethane product is initiated, it is desirable before conducting either of the above two processes to determine the temperature at which thermal decomposition begins to occur in the particular decabromodiphenylethane product being used. This can be done by use of Differential Scanning Calorimetry (DSC), preferably conducted with prolonged heating and slow increases in temperature. Generally speaking, decabromodiphenylethane products assaying about or above about 98 GC area percent of decabromodiphenylethane itself may be heated at about 220° C. to about 230° C. without initiation of thermal decomposition. However, to ensure reliable results, temperatures as high as 250° C. usually should be avoided with such products.

From the above it will be seen that no precise temperature at which initiation of thermal decomposition of a decabromodiphenylethane product exists. This is because such temperature can be greatly affected by the impurity content in the product and the rate and duration of the heating. Once thermal decomposition is initiated, HBr is released and this can have an accelerating effect upon the rate of decomposition. These same principles regarding the various thermal decomposition initiation temperatures are deemed to apply to other highly brominated organic compounds.

In each of the above preferred processes (i.e., the heating-slurrying and the slurrying-heating processes) the particulate solids are recovered from the slurry by use of a physical separation procedure such as filtration, centrifugation, draining, or the like. Prior to isolating solids from the slurry, the slurry can be cooled or allowed to cool to a temperature that is lower than the temperature(s) to which the agitated slurry was exposed.

While the above heating-slurrying and the slurrying-heating processes are described in connection with treatment of decabromodiphenylethane products, the same process technology can be used to reduce the occluded bromine content of other highly brominated compounds using appropriate temperature conditions to avoid initiation of thermal decomposition of the particular brominated compound(s) being treated in the process. For example, decabromodiphenyl oxide products can be subjected to either such process. Also, either of the above two processes can be utilized for reducing the occluded bromine content of decabromodiphenylalkane products in which the alkylene bridge between the two pentabromophenyl groups contains in the range of 2 to 6 carbon atoms, and preferably in the range of 2 to 3 carbon atoms. As noted above, the process technology of this invention has been found particularly well adapted for reducing the occluded bromine content of decabromodiphenylethane products. As is well known in the art, decabromodi-phenylethane is also known as 1,2-bis(pentabromophenyl)ethane.

The process technology of this invention enables the preparation of a wide variety of highly brominated, particulate organic compounds having desirably reduced contents of occluded bromine. However, a feature of this invention is that the heating-slurrying and the slurrying-heating processes described above enable the preparation of novel decabromodiphenylethane products having a combination of properties which is deemed to render these particular products not only highly desirable for use as flame retardants, but also as new compositions of matter. Such novel products, which form additional embodiments of this invention, are described hereinafter.

The above and other embodiments of the invention will be still further apparent from the ensuing description and appended claims.

FURTHER DETAILED DESCRIPTION OF THE INVENTION

The processes of this invention can be applied to any of a wide variety of solid brominated organic compounds or mixtures of solid brominated organic compounds that have a total bromine content of about 60 wt %, preferably about 70 wt %, and more preferably about 80 wt % or more, and that contain occluded bromine. These compounds contain a plurality of bromine atom substituents on one or more aromatic rings in the compound and thus have very poor solubility in organic solvents (e.g., their solubility in bromobenzene is no more than about 2 grams per 100 mL at 160° C.). Some non-limiting examples of such compounds include hexabromobenzene, 2,3,4,5,6-pentabromotoluene, pentabromophenol, decabromobiphenyl, decabromodiphenylethane a.k.a. 1,2-bis(pentabromophenyl)ethane, decabromodiphenyl oxide, tetradecabromodiphenoxybenzene, decabromodiphenylpropane, deca-bromodiphenylbutane, decabromodiphenyl sulfide, pentadecabromo-1,3,5-triphen-ylpentane, deca-bromo-1-phenyl-3-tolyl propane, and similar brominated flame retardants that have a total bromine content of at least about 60 wt %. A mixture of two or more such compounds and a preferred mixture containing, say, at least about 90 wt % of a perbrominated aromatic hydrocarbon with the balance to 100 wt % consisting essentially of lower brominated analogs of the same compound, in which each such mixture contains occluded bromine and at least about 90 wt % of bromine substitution, can be treated pursuant to this invention. A typical example of the first type of such mixture is a mixture of decabromodiphenylethane and nonabromodiphenylethane in any proportions relative to each other. A typical example of a preferred mixture is a mixture composed of about 98 wt % of decabromodiphenyl oxide, about 1.8 wt % of nonabromodiphenyl oxide, and about 0.2 wt % or less of octabromodiphenyl oxide. Another example of a preferred mixture is a mixture composed of about 98 wt % of decabromodiphenylethane, about 1.9 wt % of nonabromodiphenylethane, and about 0.1 wt % or less of octabromodiphenylethane. Especially preferred products for treatment pursuant to this invention are decabromodiphenylethane products containing at least about 80 wt % of bromine. In all cases, the highly brominated product subjected to the process will contain at least some occluded bromine.

Methods for use in determining the total bromine content of such compounds or mixtures of compounds, and for determining the occluded bromine content of such compounds or mixtures of compounds are set forth hereinafter. Whenever necessary or desirable, such methods can be applied both to the compounds or mixtures of compounds before and after they have been subjected to a process of this invention. However it is not required that such analyses be performed in every case. For example, once the bromination conditions for run after run or for a continuous run on representative samples of the same compound produced in the same way have been established and are used, occasional or periodic analyses may be utilized to ensure that the values for total bromine and occluded bromine on subsequently produced representative samples are within specifications adopted for that product based on prior analyses.

A wide variety of inert organic liquid diluents can be used in conducting a process of this invention. The chief requirement is that the inert organic liquid diluent must not react with the brominated compound during the process to change the chemical composition of the compound—i.e., the diluent must be inert in this sense. Preferred inert organic liquid diluents are those which will dissolve or otherwise take up free elemental bromine released in the process and also at least some of the hydrogen bromide that possibly may be released in the process. This reduces the possibility of these materials (free elemental bromine and/or HBr) escaping into the atmosphere and affords the opportunity to recover such materials or reaction product(s) thereof from the inert organic liquid diluent once the levels of such materials or reaction product(s) therein become high enough (e.g., through repeated use of the same inert organic liquid diluent over time) to justify taking the steps necessary to recover one or both of such materials or reaction product(s) from the inert organic liquid diluent.

The inert organic liquid diluents used in the practice of this invention are referred to as such because the solid brominated organic compounds or mixtures of solid brominated organic compounds treated pursuant to this invention form concentrated slurries therein with only very small amounts of the slurry actually dissolving in a given inert organic liquid diluent at any given instant in time. Such inert organic liquid diluents apart from use in this invention are generally known as organic solvents as they can dissolve a wide variety of ordinary organic compounds. Non-limiting examples of types of liquid solvents for use as inert organic liquid diluents in the processes of this invention include, for example, saturated hydrocarbons, unsaturated hydrocarbons, aromatic hydrocarbons, ketones, ethers, esters, carboxylic acids, chlorocarbons, chlorohydrocarbons, bromocarbons, bromohydrocarbons (including bromoaromatic hydrocarbons), bromofluorohydrocarbons, bromochlorohydrocarbons, and alicyclic hydrocarbon compounds. Mixtures of liquid solvents, including mixtures of two or more of the same kind of solvent (e.g., two or more different saturated hydrocarbons, two or more ketones, and so on) and also mixtures of two or more different kinds of solvents (e.g., one saturated hydrocarbon and one ketone, one or more esters and one or more bromohydrocarbons, and so on) can be used, if desired.

The inert organic liquid diluents used should be in the liquid state at the temperature(s) selected for use in a given process. While inert organic liquid diluents can be used that are solids at room temperature but which become liquid at a temperature above room temperature and remain as liquids at the temperature(s) selected for use in a given process, it is preferable to employ inert organic liquid diluents which are in the liquid state at room temperature (and more preferably also at temperatures below room temperature) and at the temperature(s) selected for use in a given process. The process can be conducted under superatmospheric pressures if the inert organic liquid diluent under atmospheric pressure would boil off at the temperature(s) selected for use in a given process. Alternatively, the operation can be conducted at temperature(s) at which the inert organic liquid diluent boils provided a condensing system is employed to continuously condense and return the inert organic liquid diluent to the slurry.

A few non-limiting examples of typical inert liquids (and their approximate boiling temperatures as reported in the literature) which can be selected for use as an inert organic liquid diluent in a process of this invention include n-octane (b.p. 126° C.), 3-ethyl-3-methylpentane (b.p. 119° C.), 1,4-dimethylcyclohexane (b.p. 121° C.), 1-nonene (b.p. 150° C.), 1,3-decadiene (b.p. 168-170° C.), toluene (b.p. 110° C.), o-xylene (b.p. 144° C.), carbon tetrachloride (b.p. 77° C.), 1-bromoheptane (b.p. 179° C.), dibromomethane (b.p. 97° C.), 1,2-dibromoethane (b.p. 132° C.), chlorocyclohexane (b.p. 143° C.), bromocyclohexane (b.p. 163-165° C.), bromochloromethane (b.p. 68° C.), tribromomethane (b.p. 149° C.), dibromofluoromethane (b.p. 65° C.), cis-1,2-dichloroethylene (b.p. 60° C.), bromobenzene (b.p. 155-156° C.), o-bromotoluene (b.p. 182° C.), m-bromotoluene (b.p. 184° C.), acetone (b.p. 56° C.), butyl methyl ketone (b.p. 128° C.), cyclopentanone (b.p. 131° C.), 1,1-dichloro-2-propanone (b.p. 120° C.), diethylene glycol dimethyl ether (b.p. 162° C.), dichloroethyl ether (b.p. 179° C.), methyl ethyl ketone (b.p. 80° C.), acetic acid (b.p. 118° C.), propionic acid (b.p. 141° C.), ethyl acetate (b.p. 77° C.), perchloroethane (b.p. 138° C.), and tetrachloroethylene (b.p. 121° C.). Bromobenzene is a preferred inert organic liquid diluent for use in the processes of this invention.

The amount of the brominated organic compound(s) present in the concentrated slurries formed and utilized in the practice of this invention can vary depending upon such factors as the identity of the brominated organic compound(s) in the slurry, the identity of the component(s) serving as the inert organic liquid diluent, and the temperature at which the slurry is to be heated. Generally speaking, the concentrated slurries used in this invention will contain at least about 20 percent by volume of the brominated organic compound(s) with the remainder to 100 percent by volume usually being one or more components serving as the inert organic liquid diluent. Typically, the amounts of brominated organic compound(s) in the slurry will fall in the range of about 25 to about 70 percent by volume of the slurry.

In one embodiment of the invention a concentrated slurry of such compound in an inert organic liquid diluent is exposed to a temperature in the range of about 60 to about 230° C. (and preferably in the range of about 150 to about 160° C.) for a period of at least about 1 hour (preferably for a period of in the range of about 2 to about 3 hours, and more preferably in the range of about 4 to about 6 hours), and the solids are isolated (recovered) from the mixture. If desired, the mixture is cooled or allowed to cool to a lower temperature prior to isolating these solids. The concentrated slurry can be formed and exposed to the elevated temperature(s) by preheating the inert organic liquid diluent to a temperature in the desired range and mixing the compound(s) to be treated and the inert organic liquid diluent while the diluent is at one or more temperatures in the desired range. Another procedure for forming the concentrated slurry is to mix the compound(s) to be treated and the inert organic liquid diluent while the diluent is below a temperature in the desired range and then heating the resultant slurry with agitation to one or more temperatures in the desired range. Other variants in these procedures are possible and are within the scope of this invention. It is desirable to agitate the slurry at least during most, if not all, of the heating period, and where applicable, during the formation of the slurry as well. If desired, a reduced amount of heat energy, e.g., in progressively lower amounts, can be applied to the slurry as its temperature is decreasing. As noted above, a feature of this invention is that the process is conducted at a temperature below that at which the slurried brominated aromatic compound can dissolve to any substantial extent in the inert organic liquid diluent. Thus, the processes of this invention are performed at temperatures and in a solvent in which no more than about 5 weight percent, and preferably no more than about 3 weight percent, of the brominated aromatic compound is dissolved at any given time in the inert organic liquid diluent.

In another embodiment of the invention a concentrated slurry of the compound(s) in an inert organic liquid diluent is subjected to grinding or milling at one or more temperatures in the range of about 50 to about 160° C. (and preferably in the range of about 50 to about 100° C.) for a period of at least about 1 hour (and preferably for a period of in the range of about 2 to about 3 hours, and more preferably in the range of about 4 to about 6 hours), and optionally cooling, or enabling the resultant mixture to cool to a lower temperature. Thereafter, the solids are isolated (recovered) from the mixture, for example, by centrifugation or filtration. As in the preceding embodiment, the extent to which the brominated aromatic compound is dissolved in the inert organic liquid diluent is minimal, i.e., the inert organic liquid diluent at no point in the process contains in solution more than about 5 weight percent, and preferably no more than about 3 weight percent, of the brominated aromatic compound.

Without desiring to be bound by theory, it is postulated that in the processes of this invention the slurries undergo numerous cycles of equilibrium that are established between a small amount of dissolved brominated compound and a large amount of undissolved brominated compound during the heating of the slurry or during the grinding of the slurry with or without application of heat energy. Thus as a small increment of the total solids in the slurry dissolves, the free elemental bromine originally trapped therein as occluded bromine is released into the inert organic liquid diluent and the resultant dissolved solids are at liberty to reform as solids while a fresh small increment of other solids is dissolving to release its entrapped free elemental bromine and then reform as solids, and so on. In the grinding embodiment, the grinding facilitates the incremental dissolution and also can physically break open the particles to release entrapped free elemental bromine.

Besides release of occluded bromine, ionic bromine (i.e. bromide) salts that may be present in the initial solid brominated compound(s) can be released from the solids into the inert organic liquid diluent during the processing.

The inert organic liquid diluent can be reused or recycled to the process. When the inert organic liquid diluent contains a sufficient amount of free elemental bromine and other bromine derivatives such as ionic bromine (bromide) salts and/or HBr to make desirable the recovery of such components, the inert organic liquid diluent can be processed to recover such bromine values.

The following analytical procedures should be used for determining the following properties of solids before and/or after subjecting the solid, highly brominated aromatic organic compounds to processing pursuant to this invention. In the case of the Hunter Color Value Test, it is recommended that the solids to be used in the test be samples which have been ground. Thus samples from a commercial-sized plant are typically samples of product that have been ground in a Raymond mill, a Bepex mill, or equivalent hammer mill. Where the product to be color tested is product from a laboratory scale operation, it is recommended that the analyses be performed on samples that have been ground in a jet mill such as is available from The Jet Pulverizer Company, Inc., model 02-506. The Jet Pulverizer Company's present address is 1255 North Church Street, Moorestown N.J. 08057-1166, and their present mailing address is P.O. Box 212, Palmyra, N.J., 08065-0212. Product samples for comparative testing purposes should be ground under the same conditions whenever possible.

Determination of Total Bromine Using Schoeniger Method

Total bromine is determined by the Schoeniger method. This method involves burning in an oxygen-rich atmosphere, a sample of known weight. The liberated bromine is reduced to the bromide with sodium arsenite in a basic medium. The bromide content is determined by titrating with silver nitrate to a potentiometric and point, using a silver titrode electrode to signal the end point. The automatic potentiometric nitrator can be a Metrohm 716 or 736 titrator, or equivalent, capable of dynamic or constant millivolt titration. The silver titrode electrode is a Metrohm 6.0430.100 electrode (catalog number 2094850-7) or equivalent. A Schoeniger combustion flask with standard tapered joint stopper and platinum carrier, and a Thomas-Ogg oxygen flask infrared igniter (Arthur H. Thomas, Product No. 6516-G10) are used. If desired, a Halogen Projector Lamp, model DFN/DFC 150W-125V can be employed in place of a Thomas-Ogg oxygen flask infrared igniter. Deionized or distilled water, isopropyl alcohol, 1:1 sulfuric acid solution formed from equal volumes of concentrated sulfuric acid and deionized or distilled water, a caustic-arsenite solution formed by mixing together 60 g of NaOH and 60 g of $As_2O_3$ and 1 liter of water with stirring, 0.1N standardized silver nitrate solution, powdered cane sugar, dry compressed oxygen, and 0.1% methyl orange indicator solution in distilled water are the chemicals used in the procedure.

In conducting the Schoeniger procedure with a solid sample, an amount of 0.04 to 0.08 g of sample, weighed to 0.00001 g accuracy, on creased black filter paper is folded inside the filter paper and placed in the platinum sample holder of the Thomas-Ogg combustion flask. If the sample is a liquid, to a 0.04 to 0.08 g sample, weighed to the same accuracy, in a tared number 3 gelatin capsule, is added approximately an equal volume of powdered cane sugar, the capsule is placed in the platinum sample holder of the Thomas-Ogg combustion flask, and a black strip of paper is inserted between the capsule and the platinum sample holder. Then, the following steps are taken: (a) To the combustion flask add 15 mL of caustic arsenite solution and 3 drops of ammonium hydroxide, (b) Flush the flask thoroughly for at least two minutes with oxygen. Liberally apply silicone grease to the stopper/sample holders, place holder in the top of the flask and flush for at least one more minute. Stopper the flask with the stopper onto which the platinum carrier with the weighed sample is attached, and secure so that the flask is gas tight when inverted. The silicone grease should form a continuous seal around the entire joint surface. If any gaps are present add more grease, (c) Place the inverted combustion flask into the Thomas-Ogg oxygen flask infrared igniter, align igniter with paper, and light the sample by turning on the infrared lamp to ignite the paper, (d) As soon as the sample has burned, swirl contents of the flask several times to coat the inside walls, (e) Allow the flask to stand for 30 minutes while shaking the flask frequently during the first five or six minutes and occasionally for the last twenty minutes, (f) Rinse the platinum sample carrier and the inside walls of the flask thoroughly with deionized or distilled water. Add 1 pellet of KOH, 2 drops of methyl orange indicator, and 5-6 boiling stones. Bring to boil and evaporated excess water until volume is about 40-50 mL, (g) Quantitatively transfer the contents of the flask into a 200 mL tall form beaker. The total volume of sample and rinsing should be approximately 100-120 mL. Follow with two to three 10 mL rinses using IPA, (h) Drop in a magnetic stirring bar and place the beaker on a magnetic stirrer. Acidify to pink endpoint with 10 mL of 1:1 $H_2SO_4$. If the solution is still yellow add additional 5 mL aliquots of 1:1 $H_2SO_4$ as needed to reach a pink endpoint. Dissolved $CO_2$ will be liberated as the acid is added, (i) Introduce the silver titrode into the sample, and titrate with 0.1 or 0.01 N $AgNO_3$ on the autotitrator according to manufacturer's instructions, (j) Run a blank through all above steps, omitting only the sample, and (k) Calculate weight % Bromide.

$$\% \text{ Br} = \frac{(S - B)(N)(7.9904)}{\text{Sample Weight in Grams}}$$

where S is the milliliters of silver nitrate required to titrate the sample, B is the milliliters of silver nitrate required to titrate the blank, and N is the normality of the silver nitrate solution.

Determination of Free Bromine and Ionic Bromine

At the outset, it is worth mentioning that those of skill in the art sometimes refer to the occluded bromine in the product particles as free bromine.

In brief, the procedure used to determine occluded bromine and/or ionic bromine (bromide) of decabromodiphenylethane is as follows: The sample is dissolved in 1,2,4-trichlorobenzene to release the occluded bromine and bromide. The bromine is then reduced to bromide by the addition of an aqueous sodium sulfite solution. The bromide is extracted into the aqueous phase and determined by ion chromatography. The total of occluded bromine and bromide is calculated from this result. To determine the occluded bromine the same procedure is repeated without using sodium sulfite. The bromide from the free bromine in the sample and bromide formed from hydrolysis of occluded bromine is extracted into the aqueous phase and determined by ion chromatography. The occluded bromine content is estimated from this uncorrected ionic bromide result and the total free elemental bromine and bromide result. About one half of the occluded bromine is converted to bromide at low bromine levels in accordance with the equation:

$$Br_2 + H_2O \Longrightarrow HBr + HOBr$$

Therefore, the occluded bromine is estimated as follows:

ppm free elemental bromine=2×(ppm total of free elemental bromine and bromide−ppm of uncorrected ionic bromide).

The ionic bromine is estimated as follows:

ppm of ionic bromine=ppm total occluded bromine and bromide−ppm of occluded bromine.

In greater detail, the apparatus and procedure used to determine occluded bromine and/or ionic bromine (bromide) in decabromodiphenylethane is as follows:

A) The required equipment includes a Dionex DX-500 ion chromatograph or equivalent, equipped with a conductivity detector; a Dionex PeakNet chromatography data collection and processing system and a Dionex IonPac® AS11-HC column equipped with Dionex IonPac® AG11-HC guard column.

B) The ion chromatographic operating conditions involve (a) as eluent: EG40 KOH gradient, (b) flow-rate: 1.5 mL/min, (c) injection volume: 25 μL, (d) detector range: 200 μS, (e) suppressor: ASRS-Ultra 4 mm, (f) suppressor current: 100 mA, and (g) regenerant: Autosuppression recycle mode.

C.) The EG40 operating conditions are as listed in the following table.

| Time | Condition | Concentration |
|---|---|---|
| −7.100 | Concentration = | 30.00 |
| −7.00 | Concentration = | 5.00 |
| −1.200 | Autosampler Closed | |
| 0.000 | ECD. Autozero Concentration = | 5.00 |
| | Inject Position ECD_1.AcqOn Concentration = | 5.00 |
| 28.000 | Concentration = | 30.00 |
| 28.00 | ECD_1.AcqOff Concentration = | 30.00 |
| | Wait | Ready |

D) The required chemicals are (a) deionized water with a specific resistivity of 17.8 megohm-cm or greater, (b) 1,2,4-trichlorobenzene, HPLC grade, (c) sodium sulfite, reagent grade and (d) 0.1 wt % solution of sodium sulfite in water.

E) For standardization quality control, a standard solution "B" is prepared as follows: A concentrated bromide standard solution (1,000 μg/mL) is prepared by weighing 0.1287 g of sodium bromide into a 100-mL volumetric flask, diluting to volume with deionized water and mixing well. This is standard solution "A". The bromide calibration standard solution "B" is prepared by pipetting 100 μL of the concentrated bromide standard solution into a 100-mL volumetric flask which is then filed to volume with deionized water and mixed well. This provides a standard solution "B" of 1 μg/mL as bromide. Two aliquots of the latter bromide calibration standard solution are loaded into individual polyseal autosampler vials for duplicate analysis.

F) In conducting the analyses it is recommended to prepare duplicate samples for both the occluded bromine/bromide determination and for the uncorrected ionic bromine (bromide) determination, so that a total of four sample preparations is used for each sample that is analyzed. The detailed analytical procedure involves the following: (a) Approximately 0.030 g of the sample is weighed into a 40-mL amber glass EPA vial. (b) 20 mL of 1,2,4-trichlorobenzene is added to the vial using a volumetric pipet, the vial is capped tightly with the septum cap and the vial is shaken slightly and sonicated to wet the sample. (c) A blank is prepared as above containing only 20 mL of 1,2,4-trichlorobenzene. (d) The vials are placed in a heating block at approximately 95° C. for 10 minutes with occasional shaking until the sample has dissolved. (e) For determining ionic bromine (bromide), the vial is removed from the bath and exactly 5 mL of deionized water is immediately added through the septum cap by means of a syringe. The vial remains sealed. (f) For determining total occluded bromine and bromide the vial is removed from the bath and exactly 5 mL of sodium sulfite solution in deionized water is immediately added through the septum cap by means of a syringe. The vial remains sealed. (g) Each vial is shaken on a shaker for 20 minutes. (h) Using a disposable pipet, the upper aqueous layer is removed and filtered through a GHP Polypro syringe filter. (i) 25 μL of the filtered sample is injected into the ion chromatograph and analyzed using the above operating conditions.

G) The calculations used are as follows:
a) This method uses the response factor calculated from duplicate injections of the individual standard solution "B". The response factor is calculated using the equation:

$$RF = \frac{Avg.\, Peak\, Area\, (2\, injections)}{Standard\, Concentration\, (\mu g/mL)}$$

b) The area of the bromide peak for each sample run is corrected for the area of the bromide peak in the blank in accordance with the expression:

$$A_S - A_b = A$$

where: $A_S$ is the area of the sample peak; $A_b$ is the area of the blank peak;

and A is the corrected area of the sample peak.

c) The corrected bromide area for each sample preparation is used to determine the total concentration of occluded bromine and bromide in the sample using the expression:

$$ppm\, Br = \frac{A \times V}{RF \times W}$$

where A is the corrected area of the sample, RF is the response factor for bromide, W is the amount of sample expressed in grams (approximately 0.03 g) and V is the total volume of the aqueous solution (5 mL).

d) The levels of occluded bromine and ionic bromine (bromide) are calculated from the duplicate average results for total occluded bromine and bromide (sulfite treated) and for uncorrected ionic bromine (no sulfite) using the expression:

ppm occluded bromine=2×(ppm of total occluded bromine and bromide)−(ppm uncorrected bromine).

Hunter Color Value Test

Hunter Color Value determinations are conducted using a HunterLab ColorQuest XE spectrophotometer with appropriate sample devices. The instrument should be standardized for recommended single-number index and the large area of view, first using the light trap then the white standard tile that comes with the instrument. After standardization, the procedure used is as follows:

A) Lower or remove the sample clamp. Install the shelf of the reflectance sample shelf with light cover (HunterLab Part Number B02-1005-172) at the reflectance port.

B) Scoop up powder from the sample batch and fill the 50-mm glass cell (HunterLab Part Number 13-8573-20) to the top. The 2-inch (50-mm) sample thickness makes the translucent powder effectively opaque for reflectance measurements.

C) Tap the sample cup once on a hard surface to settle the loose powder and then place the filled cell flush against the reflectance port so that the powder will be red through the clear glass window of the cell.

D) Cover the sample cell with the opaque cover. The cover minimizes the possibility of ambient light reaching the detector through the powder sample when the measurement is taken.

E) Take a single color reading of the powder. Dump, refill, and read the powder at least three times from the same batch. Average the three color reading for a single color measurement representing the color of the batch. Averaging multiple readings minimizes measurement variation associated with non-uniform samples.

F) Record the average color values for the sample batch.

G) Use ASTM procedure D 1925-87 to calculate Yellowness Index (YI).

Mean Particle Size Determination

To determine mean (average) particle size, a Coulter LS-250 counter or equivalent is used. In employing this Coulter counter its small volume module is used. The operating instructions of the manufacturer are followed. Alternatively, a Horiba laser light scattering instrument (e.g., Horiba LA900 Model 7991) or equivalent can be used. The procedure involves weighing the powdery sample, typically an amount in the range of about 0.01 gram to about 0.015 gram, into a clean dry aluminum cup that has been washed with deionized water before use. The instrument autosampler disperses the sample in water using a dispersant and ultrasonic treatment. This suspension is circulated through a measuring cell where the powder particles scatter a beam of laser light. Detectors in the instrument measure intensity of the light scattered. The computer in the instrument calculates both average particle size and particle size distribution from such measurements. Typically, 10 separate representative samples of a given powdery substance are subjected to the test. An alternative instrument which has been successfully employed is a Coulter LS-230 instrument using its small volume module.

Melting Point Determination

Melting Point determinations are conducted using a Differential Scanning Calorimeter (DSC) method. The principal equipment used is a TA Instruments Model 2910 DSC with its standard DSC cell and Thermal Analyst 5000 PC controller, or equivalent, and a Gas Flowmeter such as Sierra Instruments Model A-2960, or equivalent. The DSC should have been recently calibrated for baseline slope and offset, cell constant, and temperature scale using a heating rate of 10° C./min and a nitrogen gas purge rate of 50 cc/min as indicated in the DSC Operator's Manual. The procedure for the melting point determination involves heating in the DSC, a 2 to 5 mg sample of the test material at 2° C./min through the melt endotherm of the test material. The Universal Analysis software option of the Thermal Analyst 5000 PC controller is used to display the DSC trace. The melt endotherm is integrated using the sigmoidal baseline option. The parameter of interest is the extrapolated onset temperature, which is the temperature at the intersection of the baseline with a tangent drawn at the point of maximum slope on the leading edge of the endotherm peak. This value is taken as the melt point. If multiple peaks are present, the results for the individual peaks should be reported. If individual peaks are poorly resolved, graphical methods such as "perpendicular drop line construction" are used to associate areas of the melt endotherm with individual peaks.

Determination of Decabromodiphenylethane Product Assay

To obtain a GC assay of a decabromodiphenylethane product, the following procedure should be used:

A) The required equipment includes a Hewlett/Packard 5890 Series II gas chromatograph or equivalent, equipped with a flame ionization detector, a cool on-column temperature and pressure programmable inlet, and temperature programming capability, and a Hewlett/Packard 7678 or equivalent automatic injector. A Hewlett/Packard 3396 A integrator or chromatographic data system such as VG's Multichrom or equivalent is used for data acquisition and analysis. The gas chromatographic column is a fused silica open-tubular, high-temperature aluminum clad 12M×0.53 mm, 0.15µ film thickness capillary column (SGE 12QCS/HT5-0, 15; catalog number 051585).

B) The chemicals used in the procedure are dibromomethane (99%); helium, zero grade; hydrogen, zero grade; and air, zero grade. The conditions for the gas chromatograph are (a) detector temperature: 350° C.; (b) inlet temperature; 70° C., 125° C./min to 350° C., hold to end of run; (c) carrier gas helium at 10 mL/min; (d) inlet pressure: 4.0 psig (ca. 1.29×10$^5$ Pa; at 10 mL/min), 0.25 psi/min to 9.0 psig (ca. 1.63×10$^5$ Pa), hold to end of run; (e) oven temperature: 60° C., 12° C./min to 350° C., hold for 10 minutes; (f) injection mode: cool on-column; and (g) injection volume: 2.0 μL.

C) The procedure involves the following steps: (a) set up the gas chromatograph conditions as described above. Put 1 mL of dibromomethane in a crimp top vial and seal it up. Place the dibromomethane on the auto injector and inject it into the gas chromatograph to insure a clean system; (b) weigh 0.003 gram of decabromodiphenylethane sample into a 15 mL glass vial; (c) add enough dibromomethane to bring the sample weight up to 10 grams; (d) cap the vial and shake well; (e) place the vial containing the sample into a sample block on a hotplate which is at approximately 90° C. Loosen the cap of the vial slightly to prevent pressure build up in the vial. Place a 2 mL crimp top vial on the hotplate at the same time that the sample is placed on the hotplate; (f) after one hour check the sample and be certain that it is completely dissolved; (g) transfer the sample into the heated crimp top vial and seal it in the vial; and (h) as rapidly as possible place the sample on the auto injector and inject the sample into the gas chromatograph. It is important to inject the sample warm, as the decabromodiphenylethane will come out of solution as the sample cools.

D) Results are reported as area % for decabromodiphenylethane and impurities. Percent bromine is determined by the area % of the constituents as determined by the method, and known bromine content of each compound. For example, pure decabromodiphenylethane has 82.27 wt % bromine, and pure nonabromodiphenylethane has 80.59 wt % bromine.

Novel decabromodiphenylethane products producible and provided by this invention are characterized by having an occluded bromine content in the range of zero to about 105 ppm, a mean particle size of at least about 180 microns, a Hunter Color L value, using an unground sample, of at least about 83, and a Hunter Yellowness Index, using an unground sample, of about 30 or less. Preferred novel decabromodiphenylethanes of this invention additionally have at least one of the following properties utilizing analytical procedures described herein:

1) A decabromodiphenylethane assay by gas chromatography in the range of about 98 to about 99.9 area %.

2) A DSC melting temperature in the range of about 350 to about 360° C.

3) A content of ionic bromine (bromide) of less than about 170, more preferably in the range of about 50 to about 165 ppm.

Decabromodiphenylethane products possessing additional property 1) are more preferred, and decabromodiphenylethane products possessing additional properties 1) and 2); or 1) and 3); or 2) and 3) are still more preferred. Even more preferred are decabromodiphenylethane products having all three of additional properties 1), 2) and 3).

The following Examples illustrate but are not intended to limit the invention to only what is described therein. In Examples 1-4, decabromodiphenylethane obtained from wet filter cake of product formed by bromination of 1,2-diphenylethane in accordance with the disclosure of U.S. Pat. No. 6,518,468 that was not subjected to the drying and grinding or oven-aging procedures described therein was used as the illustrative starting material. Utilizing the above-described analytical procedures, this wet cake product contained 810 ppm of occluded free elemental bromine and 269 ppm of ionic bromine (bromide). The Hunter color values (wherein YI stands for Yellowness Index) obtained without standard grinding of the product were:

| L | 80.61 |
|---|---|
| a | 6.39. |
| b | 24.36 |
| YI | 60.04 |

Hunter color values are dependant on the actual particle size. The smaller the particle size, the lower is the yellowness index (YI) and higher the L (lightness index). All color values reported herein are for unground samples of decabromodiphenylethane.

Example 1

A concentrated slurry of a portion of the above decabromodiphenylethane and acetone was formed by mixing the decabromodiphenylethane and acetone in proportions of 30 wt % of decabromodiphenylethane and 70 wt % of acetone. The slurry was heated and maintained at reflux (ca. 59° C.) for 4.5 hours and then promptly cooled to room temperature (ca. 25° C.) and filtered to recover the solids. The solids were dried at 25° C. and subjected to analyses. The data from the analyses are summarized in Table I.

Example 2

The procedure of Example 1 was repeated except that the concentrated slurry was formed from another portion of the same decabromodiphenylethane and toluene in proportions of 28 wt % of the decabromodiphenylethane and 72 wt % of toluene. The data from the analyses on the dried solids from this experiment are summarized in Table I.

Example 3

The procedure of Example 1 was again repeated except that in this case the concentrated slurry was formed from still another portion of the same decabromodiphenylethane and bromobenzene in proportions of 18 wt % of decabromodiphenylethane and 82 wt % of bromobenzene. The data from the analyses on the dried solids from this experiment are summarized in Table I.

Example 4

The procedure of Example 1 was again repeated except that in this case the concentrated slurry was formed from yet another portion of the same decabromodiphenylethane and bromobenzene in proportions of 18 wt % of decabromodiphenylethane and 82 wt % of bromobenzene and the concentrated slurry was held at reflux for 14 hours. The data from the analyses on the dried solids from this experiment are summarized in Table I. In Table I, the term "Free Bromine" refers to free elemental bromine that is occluded in the product.

TABLE I

| Property | Units | Untreated Dried Wet Cake | Product from Example 1 | Product from Example 2 | Product from Example 3 | Product from Example 4 |
|---|---|---|---|---|---|---|
| Free Bromine | ppm (wt/wt) | 810 | 364 | 226 | 186 | 129 |
| Ionic Bromine (Bromide) | ppm (wt/wt) | 269 | 512 | 601 | 307 | 271 |
| Hunter Color | L | 80.61 | 82.23 | 82.83 | 84.86 | 81.86 |
| | a | 6.39 | 4.96 | 5.35 | 3.55 | 1.5 |
| | b | 24.36 | 21.06 | 21.92 | 19.40 | 15.83 |
| | YI | 60.04 | 50.44 | 52.26 | 44.30 | 35.83 |

It will be noted from the above results that reductions in occluded bromine contents of the decabromodiphenylethane were achieved. Similar results on free bromine and ionic bromine are expected when utilizing an embodiment of this invention involving grinding of the concentrated slurry of the decabromodiphenylethane. The grinding should further improve the Hunter Color values.

Similar or comparable reductions in occluded bromine contents of other solid, highly brominated aromatic organic compounds are deemed achievable by the practice of this invention under appropriate conditions.

Example 5

A sample of decabromodiphenylethane wet cake as produced in a commercial plant facility for the production of Saytex® 8010 flame retardant (Albemarle Corporation) was obtained and divided into two parts. One part of the sample was heated at 200° C. for six hours in an oven and the other part was heated at 230° C. for six hours in an oven. Two 100 gram samples were taken from each of the two heated samples giving a total of four individual 100 gram samples. One of the individual samples that had been heated at 200° C. and one of the individual samples that had been heated at 230° C. were then stirred each as an individual slurry with 300 mL of bromobenzene at 156-158° C. for six hours, followed by filtration and drying at 160° C. for 6 hours to remove bromobenzene. The other two samples that had been heated at 200° C. and 230° C., respectively, were not subjected to the slurrying process of this invention. Selected physical properties were then measured for each of the four samples in order to assess differences in physical properties. The results are given below in Table II in which the abbreviated terms used have the following meanings: Mean PS denotes mean (i.e. average) particle size; Free Br2 denotes free elemental bromine that is occluded in the product; and Ionics denotes ionic bromine (bromide). The Hunter Color values are reported in the normal fashion using unground samples.

TABLE II

| | Heating Temperature 200° C. | | Heating Temperature 230° C. | |
|---|---|---|---|---|
| | Not slurried | Slurried | Not slurried | Slurried |
| Hunter color | | | | |
| L | 81.36 | 86.57 | 76.93 | 83.16 |
| a | 1.72 | 0.85 | 2.35 | 1.78 |
| b | 16.85 | 13.32 | 11.23 | 8.87 |
| YI | 38.85 | 28.52 | 28.60 | 20.48 |
| Mean PS (u) | 96.81 | 278.2 | 105.3 | 182.7 |
| Free Br2 | 252 ppm | 102 ppm | 34 ppm | 0 ppm |
| Ionics (ppm) | 474 ppm | 113 ppm | 453 ppm | 162 ppm |

As seen from the data in Table II, the combination of heating to a suitable elevated temperature followed by slurrying improved the Hunter Color L values, decreased the Yellowness Index values, increased the mean particle size, decreased the free bromine content, and decreased the content of ionics. The increase in mean particle size translates in part to a reduction in the content of fines, which in turn improves the handling properties of the product and reduces the likelihood of dust formation.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

As used herein, the expression "at least about 1 hour" means the same thing as "about 1 hour or more". The same applies to other instances where the phrase "at least about" may appear.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

That which is claimed is:

1. A process of reducing the content of occluded bromine in at least one particulate brominated diphenyl alkane compound, the alkylene bridge between the two pentabromophenyl groups contains in the range of 2 to 6 carbon atoms, wherein such compound was prepared by a process including bromination in a liquid phase consisting essentially of excess bromine, has a total bromine content of at least about 60 wt % and contains an initial amount of occluded bromine in an amount greater than 105 ppm, which process comprises heating for a period of at least about 1 hour, a concentrated agitated slurry consisting essentially of such debrominated diphenyl alkane compound(s), in an inert organic liquid diluent at one or more temperatures in the range of about 60° C. up to the temperature that is just below the temperature at which thermal decomposition of said at least one particulate debrominated diphenyl alkane compound begins to occur, the occluded bromine content of the resultant solids being reduced to a final amount of occluded bromine in the process, the amount of dissolved brominated organic compound being treated in the process not exceeding about 5 wt % in the slurry at any time during said period, without grinding or milling such compound during said heating in order to reduce its particle size, wherein said final amount of occluded bromine is in the range of from about 0 to about 105 ppm.

2. A process as in claim 1 wherein the particulate debrominated diphenyl alkane compound subjected to said process initially has a total bromine content of at least about 70 wt % and wherein said slurry contains during said period no more than about 3 wt % of the dissolved brominated organic compound being treated in the process.

3. A process as in claim 1 wherein a decabromodiphenylethane product is subjected to said process.

4. A process as in claim 1 wherein, prior to conducting said process, said at least one particulate brominated diphenyl alkane compound that has a total bromine content of at least about 60 wt % and that contains occluded bromine is heated while in the form of a particulate solid-state compound in the absence of solvent at a temperature in the range of about 150 to about 230° C. for a period in the range of about 1 to about 6 hours and is then subjected to the process as specified in claim 1.

5. A process as in claim 1 wherein, after conducting said process as specified in claim 1, said at least one particulate brominated diphenyl alkane compound that has a total bromine content of at least about 60 wt % and that still contains some occluded bromine is heated while in the form of a particulate solid-state compound in the absence of solvent at a temperature in the range of about 150 to about 230° C. for a period in the range of about 1 to about 6 hours.

6. A process of preparing a decabromodiphenylethane product wherein such product has a reduced content of occluded bromine and has a combination of improved properties, which process comprises:

heating the particulate solid-state decabromodiphenylethane product, which has been prepared by a process including bromination in a liquid phase consisting essentially of excess bromine, and which has an occluded bromine content greater than about 105 ppm in the absence of solvent at a temperature in the range of about 150 to about 230° C. and for a period of at least about 1 hour; and forming from decabromodiphenylethane product that was subjected to said heating, a concentrated agitated slurry in an inert organic liquid diluent at one or more temperatures in the range of about 60° C. up to the temperature that is just below the temperature at which thermal decomposition of the decabromodiphenylethane product begins, the occluded bromine content of the resultant solids being reduced in the process, said slurry containing during said period no more than about 5 wt % of dissolved decabromodiphenylethane product being treated in the process, without grinding or milling such product in order to reduce its particle size.

7. A process as in claim 6 wherein the heated particulate solid-state decabromodiphenylethane product is cooled or allowed to cool before forming said concentrated slurry.

8. A process of preparing a decabromodiphenylethane product wherein such product has a reduced content of occluded bromine and has a combination of improved properties, which process comprises:

forming from decabromodiphenylethane product, said product having an occluded bromine content greater than about 105 ppm, a concentrated agitated slurry in an inert organic liquid diluent and heating such slurry at one or more temperatures in the range of about 60° C. up to the temperature that is just below the temperature at which thermal decomposition of the decabromodiphenylethane product begins, the occluded bromine content of the resultant particulate solids being reduced in the process, said slurry containing during said period no more than about 5 wt % of dissolved decabromodiphenylethane product being treated in the process; and recovering resultant particulate solids from the slurry and heating such particulate solids in the absence of solvent at a temperature in the range of about 150 to about 230° C. and for a period of at least about 1 hour, without grinding or milling such product during said heating in order to reduce its particle size.

9. A process as in any of claims 3-8 wherein the slurry contains during said period no more than about 3 wt % of dissolved product being treated in the process.

10. A process as in any of claims 1-2 and 3-8 wherein about 50 wt % or more of the inert organic liquid diluent is a liquid bromoaromatic hydrocarbon.

11. A process as in claim 10 wherein said liquid bromoaromatic hydrocarbon comprises bromobenzene.

12. A decabromodiphenylethane product formed by brominating diphenylethane in a liquid phase consisting essentially of excess bromine, decabromodiphenylethane product characterized by having a decabromodiphenylethane assay by gas chromatography in the range of about 98 to about 99.9 area %, an occluded bromine content in the range of zero to about 110 ppm, a mean particle size, without grinding, of at least about 180 microns, a Hunter Color L value, using an unground sample, of at least about 83, and a Hunter Yellowness Index, using an unground sample, of about 30 or less.

13. A decabromodiphenylethane product as in claim 12 further characterized by having (i) a DSC melting temperature in the range of about 350 to about 360° C., and (ii) a content of ionic bromine (bromide) of less than about 170 ppm.

14. A decabromodiphenylethane product as in claim 13 further characterized by having a DSC melting temperature in the range of about 350 to about 360° C.

15. A decabromodiphenylethane product as in claim 13 further characterized by having a content of ionic bromine (bromide) of less than about 170 ppm.

16. A decabromodiphenylethane product as in claim 15 wherein said content of ionic bromine is in the range of about 50 to about 165 ppm.

* * * * *